United States Patent
Ko et al.

(10) Patent No.: US 8,273,567 B2
(45) Date of Patent: Sep. 25, 2012

(54) PORTABLE MEASUREMENT SYSTEM HAVING BIOPHOTONIC SENSOR

(75) Inventors: Hyun Sung Ko, Seoul (KR); Chul Huh, Daejeon (KR); Kyung Hyun Kim, Daejeon (KR); Jong Cheol Hong, Daejeon (KR); Wan Joong Kim, Goyang (KR); Gun Yong Sung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 186 days.

(21) Appl. No.: 12/743,883

(22) PCT Filed: May 16, 2008

(86) PCT No.: PCT/KR2008/002761
§ 371 (c)(1),
(2), (4) Date: May 20, 2010

(87) PCT Pub. No.: WO2009/075422
PCT Pub. Date: Jun. 18, 2009

(65) Prior Publication Data
US 2010/0260643 A1    Oct. 14, 2010

(30) Foreign Application Priority Data
Dec. 13, 2007    (KR) .................. 10-2007-0130078

(51) Int. Cl.
C12M 1/34      (2006.01)
C12M 1/36      (2006.01)
G01N 21/00     (2006.01)
G01N 21/64     (2006.01)
G01N 21/25     (2006.01)

(52) U.S. Cl. ....... 435/288.7; 435/3; 435/7.1; 435/286.1; 435/287.1; 435/287.2; 422/82.05; 422/82.08; 422/82.09; 356/301; 356/318; 356/417; 356/456; 506/35; 250/458.1

(58) Field of Classification Search ............... None
See application file for complete search history.

(56) References Cited

U.S. PATENT DOCUMENTS

| | | | |
|---|---|---|---|
| 5,198,369 A | 3/1993 | Itoh et al. | |
| 5,331,958 A | 7/1994 | Oppenheimer | |
| 5,981,956 A * | 11/1999 | Stern ........................ | 506/35 |
| 7,023,544 B2 | 4/2006 | Cunningham et al. | |

(Continued)

FOREIGN PATENT DOCUMENTS
JP    09-096603 A    4/1997
(Continued)

OTHER PUBLICATIONS

Carlos F. R. Mateus et al., "Compact Label-Free Biosensor Using VCSEL-Based Measurement System," IEEE Photonics Technology Letters, Jul. 2004, pp. 1712-1714. vol. 16, No. 7, IEEE.

(Continued)

Primary Examiner — Neil N Turk (57) ABSTRACT

There is provided a portable measuring system having a biophotonic sensor. The portable measuring system also includes a tunable light source, an output intensity detector and an output wavelength detector, which are mounted therein. The portable measuring system can precisely measure a variation in the reflectivity spectrum and/or the transmittance spectrum of the biophotonic sensor before and after an antigen-antibody reaction by varying the wavelength of the tunable light source. Thus, the concentration of the antigen is precisely measured.

16 Claims, 8 Drawing Sheets

U.S. PATENT DOCUMENTS

2004/0223881 A1  11/2004  Cunningham et al.
2006/0078929 A1*  4/2006  Bickel et al. .................. 435/6
2006/0263777 A1*  11/2006  Tong ............................. 435/6
2007/0247620 A1*  10/2007  Koo .............................. 356/301

FOREIGN PATENT DOCUMENTS

JP        2000-146693 A     5/2000

OTHER PUBLICATIONS

International Search Report for PCT/KR2008/002761 filed May 16, 2008.

Written Opinion of the International Searching Authority for PCT/KR2008/002761 filed May 16, 2008.

* cited by examiner

PORTABLE MEASUREMENT SYSTEM HAVING BIOPHOTONIC SENSOR

TECHNICAL FIELD

The present invention relates to a portable measuring system having a biophotonic sensor. More particularly, the present invention relates to a portable measuring system, which can precisely measure the reflectivity spectrum or the transmittance spectrum of a biophotonic sensor mounted therein using a miniature wavemeter capable of precisely measuring the wavelength of a light source, which is applied to the bio-photonic sensor.

This work related to the present invention was supported by IT R&D Program of MIC/IITA [2006-S007-02, Ubiquitous Health Monitoring Module System Development].

BACKGROUND ART

A measuring system having a biophotonic sensor is a device that detects a specific antigen based upon the optical properties of the biophotonic sensor. In the biophotonic sensor, an antibody of an antigen is immobilized. When a blood plasma or a liquid containing the antigen is introduced to the biophotonic sensor, the antigen combines with the antibody in the biophotonic sensor, thereby changing the optical properties of the biophotonic sensor.

Below, it will be described of a process of producing the concentration of an antigen using the properties of a biophotonic sensor as above. First, the transmittance spectrum and/or the reflectivity spectrum of the biophotonic sensor prior to an antigen-antibody reaction are measured. The measured value is compared with the transmittance spectrum and/or the reflectivity spectrum of the biophotonic sensor after the antigen-antibody reaction. The comparison result is used as a basis to determine whether or not a specific antigen is present and to measure the concentration of the antigen if present.

Figure 1:
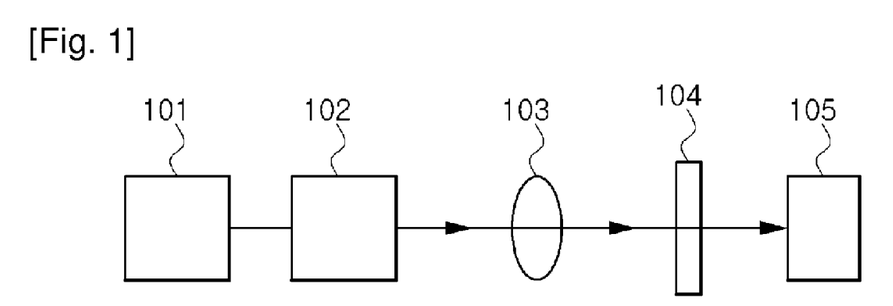
FIG. 1 is a construction view illustrating an example of conventional measuring system having a biophotonic sensor.

FIG. 1 is a construction view illustrating an example of conventional measuring system having a biophotonic sensor, which measures a transmittance spectrum using a tunable light source. Referring to FIG. 1, the conventional measuring system includes a wavelength tuner 101, a tunable light source 102, a lens 103, a biophotonic sensor 104 and a photodiode 105.

The conventional measuring system converts light from the tunable light source 102 into parallel light using the lens 103. When the parallel light transmits the biophotonic sensor 104, the conventional measuring system detects the light at the photodiode 105, thereby measuring the transmittance spectrum of the biophotonic sensor 104. The intensity and the wavelength of the light outputted from the tunable light source 102 are tuned by the wavelength tuner 101. In the biophotonic sensor 104, an antibody of an antigen is immobilized, and an antigen-antibody reaction changes the transmittance of light.

Accordingly, this type of conventional measuring system measures the optical transmittance spectrum of the biophotonic sensor 104 with respect to the output wavelength of the tunable light source using the photodiode 105.

Figure 2:
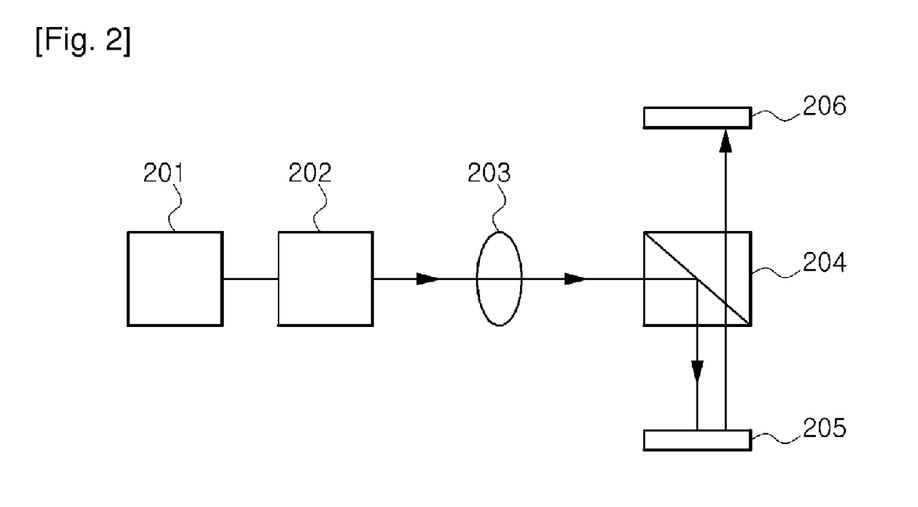
FIG. 2 is a construction view illustrating another example of conventional measuring system having a biophotonic sensor.

FIG. 2 is a construction view illustrating another example of conventional measuring system having a biophotonic sensor, which measures a reflectivity spectrum using a tunable light source. Referring to FIG. 2, the conventional measuring system includes a wavelength tuner 201, a tunable light source 202, a lens 203, a beam splitter 204, a bio-photonic sensor 205 and a photodiode 206.

The measuring system converts light from the tunable light source 202 into parallel light through the lens 203, and causes the parallel light to be reflected from the beam splitter 204 to the biophotonic sensor 205. The light reflected from the beam splitter 204 is reflected again from the biophotonic sensor 205 to the photodiode 206, which detects the intensity of the reflected light, thereby measuring the reflectivity of the beam splitter. The output wavelength of the tunable light source 202 is tuned by the wavelength tuner 201. In the biophotonic sensor 204, an antibody of an antigen is immobilized, and an antigen-antibody reaction changes the reflectivity spectrum of light.

Accordingly, this type of conventional measuring system measures the optical reflectivity spectrum of the biophotonic sensor 205 with respect to the output wavelength of the tunable light source 202 using the photodiode 206, acquires the difference in the wavelength of the biophotonic sensor 205 before and after the antigen-antibody reaction using the measurement result, and measures the concentration of the antigen.

Figure 3:
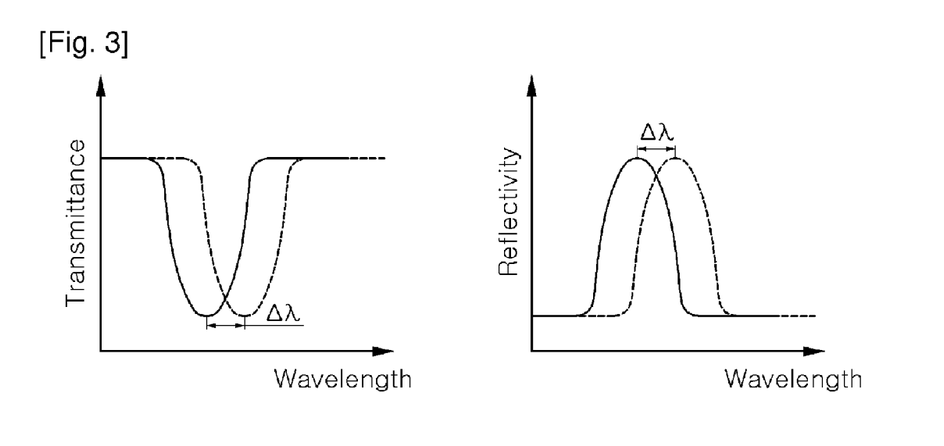
FIG. 3 is graphs illustrating the transmittances and the reflectivity spectra of typical biophotonic sensors, which are measured in the conventional measuring systems shown in FIGS. 1 and 2.

FIG. 3 is graphs illustrating the transmittances and the reflectivity spectra of the typical biophotonic sensors 104 and 205, which are measured in the conventional measuring systems shown in FIGS. 1 and 2. Referring to FIG. 3, solid lines indicate the measurement results of the biophotonic sensors 104 and 205 before the antigen-antibody reaction, and dotted lines indicate the measurement results of the biophotonic sensors 104 and 205 after the antigen-antibody reaction. Accordingly, the concentration of the antigen is measured using the difference in the wavelength $\Delta\lambda$.

In the conventional measuring systems having a biophotonic sensor as mentioned above, the presence and the concentration of an antigen are determined using the variation of the transmittance spectrum and/or reflectivity spectrum before and after the antigen-antibody reaction. It is important to precisely measure an optical power and the wavelength thereof, which are applied to the biophotonic sensor. For this, there is required a device, such as a wavemeter, which measures the optical power and the wavelength thereof, applied to the biophotonic sensor. However, this type of wavelength-measuring device is bulky and thus is not adequate to be attached to a portable system.

DISCLOSURE OF INVENTION

Technical Problem

The present invention has been made to solve the foregoing problems with the prior art, and therefore the present invention provides a portable measuring system, which can precisely measure an output wavelength of a light source using a miniature wavemeter, which is directly mounted therein, thereby precisely measuring a variation in wavelength according to a variation in the reflectivity and the transmittance spectrum of a biophotonic sensor before and after an antigen-antibody reaction.

Technical Solution

According to an aspect of the invention, the portable measuring system having a bio-photonic sensor includes a light provider emitting light; a first optical splitter splitting the light emitted from the light provider along first and second paths; an output intensity detector detecting an output intensity of the light, split along the first path; a second optical splitter splitting the light, split along the second path, along third and fourth paths; a output wavelength detector detecting an output wavelength of the light, split along the third path; a biophotonic sensor transmitting and reflecting the light split along the fourth path according to an antigen-antibody reaction; a transmittance detector detecting an intensity of the light transmitted through the biophotonic sensor; and a reflectivity detector detecting an intensity of the light reflected from the bio-photonic sensor.

The portable measuring system may further include a polarized light filter sending light of a specific polarization to the biophotonic sensor.

The light provider may include a tunable light source; a tunable light source controller supplying power to the tunable light source based upon the output intensity detected by the output intensity detector, and controlling an output wavelength of the tunable light source to be uniform using the output wavelength detected by the output wavelength detector; and a lens converting the light emitted from the tunable light source into parallel light.

The output intensity detector is a photodiode.

The output intensity detector may further include a condenser lens condensing the light split along the first path, and sending the condensed light to the photodiode.

Each of the transmittance detector and the reflectivity detector may include a photodiode measuring an intensity of the light, which is reflected from or transmitted through the biophotonic sensor. The transmittance detector or the reflectivity detector may include a condenser lens condensing the light reflected from or transmitted through the biophotonic sensor, and sending the condensed light to the photodiode.

Each of the first optical splitter and the second optical splitter may be a 1×2 type beam splitter splitting incident light by transmitting and reflecting the incident light.

The output wavelength detector may include a color filter splitting the light split along the third path, by reflecting and transmitting the light; a reflectivity detector of the color filter detecting an intensity of the light reflected from the color filter; and a transmittance detector of the color filter detecting an intensity of the light transmitted through the color filter.

Each of the reflectivity detector and the transmittance detector of the color filter may include a photodiode for detecting an intensity of light. Each of the reflectivity detector and the transmittance detector of the color filter may further include a condenser lens condensing incident light and sending the condensed light to the photodiode thereof.

The first optical splitter may include a 1×2 type first optical fiber coupler splitting incident light into two beams.

The output wavelength detector may include a wavelength division multiplexing coupler splitting the light split along the third path by the second optical splitter, along fifth and sixth paths; a second photodiode detecting an intensity of the light split along the fifth path; and a third photodiode detecting an intensity of the light split along the sixth path.

The second optical splitter may include a 1×2 type second optical fiber coupler splitting the light, from the 1×2 type first optical fiber coupler, along the third and fourth paths; and an optical fiber circulator sending the light, split along the fourth path, to the biophotonic sensor, and sending the light, reflected from the biophotonic sensor, to the reflectivity detector. Here, the portable measuring system may further include a lens for converting the light, entering the biophotonic sensor from the optical fiber circulator, into parallel light.

The second optical splitter may include a 1×2 type second optical fiber coupler splitting the light entered from the 1×2 type first optical fiber coupler, along the third and fourth paths; and a lens converting the light, split along the fourth light, into parallel light; and a 1×2 type beam splitter splitting the parallel light by transmitting and reflecting the parallel light.

Advantageous Effects

As set forth above, the portably measuring system of the present invention can precisely measure the output wavelength of the tunable light source using a miniature wavemeter mounted therein, and precisely measure the output intensity of the tunable light source using the output intensity detector. This makes it possible to precisely measure a variation in wavelength according to a variation in the transmittance spectrum and/or the reflectivity spectrum before and after the antigen-antibody reaction of the biophotonic sensor. Accordingly, the concentration of an antigen can be determined more precisely.

BEST MODE FOR CARRYING OUT THE INVENTION

Hereinafter, the present invention will be described more fully in conjunction with the accompanying drawings, in which exemplary embodiments thereof are shown, so that this disclosure will be thorough and complete, and will fully convey the scope of the present invention to those skilled in the art.

In the following description, well-known functions or constructions by a man skilled in the art are not described in detail since they would obscure the present invention in unnecessary detail.

In the drawings, the same reference numerals or letters will be used to designate like or equivalent elements having the same function.

A portable measuring system having an optical sensor of the present invention includes a light provider, first and second optical splitters, an output intensity detector, an output wavelength detector, a biophotonic sensor, a transmittance detector and a reflectivity detector. The output intensity detector detects the intensity of an output from a tunable light source, and the output wavelength detector detects an output wavelength from the tunable light source. Exemplary embodiments of the portable measuring system having an optical sensor of the present invention, which is constructed as above, will be described more fully with reference to the accompanying drawings.

Figure 4:
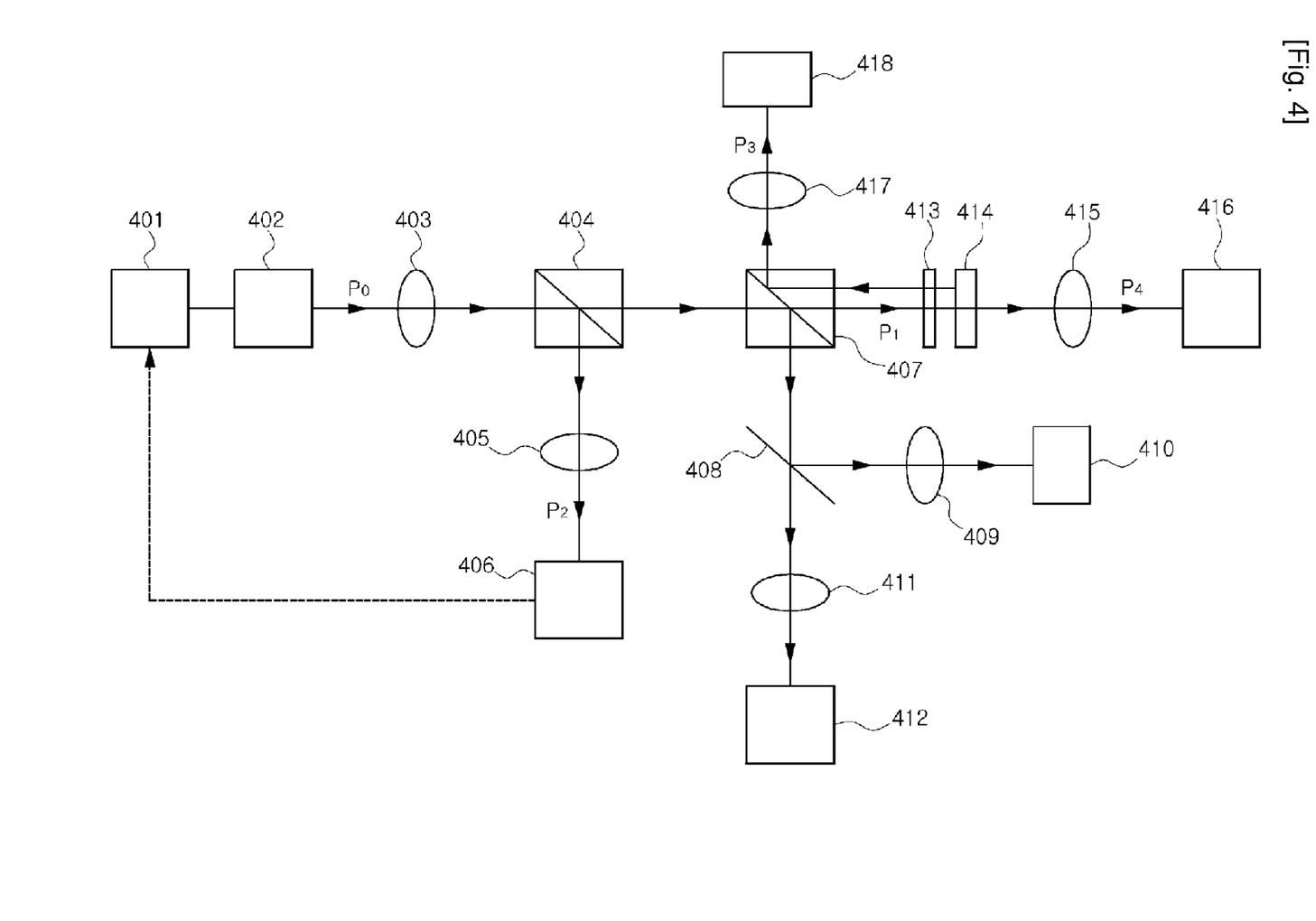
FIG. 4 is a construction view illustrating a portable measuring system having a bio-photonic sensor according to an embodiment of the present invention.

FIG. 4 is a construction view illustrating a portable measuring system having a bio-photonic sensor according to an embodiment of the present invention.

Referring to FIG. 4, the portable measuring system having a biophotonic sensor of the present invention includes a tunable light source controller 401, a tunable light source 402, first to sixth lenses 403, 405, 409, 411, 415 and 417, first and second beam splitters 404 and 407, first to fifth photodiodes 406, 410, 412, 414 and 416, a bio-photonic sensor 413, a color filter 408 and a polarized light filter 413.

The light provider includes the tunable light source controller 401, the tunable light source 402 and the first lens 403, the first and second optical splitters are the first and second beam splitters 407 and 408, the output intensity detector includes the second lens 405 and the first photodiode 406, the output wavelength detector includes the color filter 408, the third and fourth lenses 409 and 411, and the second and third photodiodes 410 and 412, and the reflectivity detector includes the sixth lens 417 and the fifth photodiode 416.

The output intensity detector serves to detect the output intensity of the tunable light source 402, and the output wavelength detector serves to detect the output wavelength of the tunable light source 402.

Specifically, the tunable light source controller 401 supplies power to the tunable light source 402, and controls the output intensity and the output wavelength of the tunable light source 402. For this, the present invention uses the output intensity detected by the first photodiode 406, and the output wavelength detected by the second and third photodiodes 410 and 412.

The tunable light source controller 401 supplies two types of power to the tunable light source 402. The first type of power determines the output intensity of light. That is, the output intensity of light from the tunable light source 402 increases in proportion to the amount of current applied to the tunable light source 402. The second type of power adjusts the output wavelength of the tunable light source 402. That is, the output wavelength is determined by the amount of current applied to the tunable light source 402.

For example, when the tunable light source 402 is a tunable laser diode using a hot wire, current applied to the hot wire generates heat, which changes the temperature of the tunable laser diode, thereby changing the output wavelength thereof. In the case where the tunable light source 402 is an external cavity laser diode, a driving motor rotates a grating mounted on the tunable laser, thereby changing the wavelength. That is, the wavelength is changed by a signal applied to a motor control circuit.

Hence, different principles of wavelength tuning may be adopted according to tunable lasers, and embodiments of the present invention are not limited to a specific type of tunable laser.

The tunable light source 402 may be implemented with any wavelength tunable light sources, such as a laser light source.

The first lens 403 converts light from the tunable light source 402 into parallel light.

The first beam splitter 404 reflects part of the parallel light, converted by the first lens 403, to the second lens 405, and transmits part of the parallel light to enter the second beam splitter 407.

The second lens 405 condenses the light, reflected from the first beam splitter 404, and sends the condensed light to the first photodiode 406.

The first photodiode 406 acquires the output intensity $P_2$ of the light, reflected from the first beam splitter 404. The output intensity $P_2$ is proportional to the output intensity of the tunable light source 402.

The second beam splitter 407 reflects part of the light, transmitted through the first beam splitter 404, toward the color filter 408 of the output wavelength detector. The second beam splitter 407 transmits the other part of the light, transmitted through the first beam splitter 404, to enter the biophotonic sensor 414 through the polarized light filter 413. $P_1$ indicates the intensity of light sent to the biophotonic sensor 414, and can be produced using the output intensity of the tunable light source 402, which is detected by the first photodiode 406, and is indicated with $P_2$.

In a typical biophotonic sensor, the transmittance spectrum and reflectivity spectrum are varied according to the polarization of incident light. The polarized light filter 413 allows light of a specific polarization to pass through. The polarization filter 413 may be omitted if the transmittance spectrum and the reflectivity spectrum of the bio-photonic sensor 414 are not polarization dependent.

The color filter 408 reflects part of the light, reflected from the second beam splitter 407, to the second photodiode 410 through the third lens 409. The color filter 408 also sends part of the light, reflected from the second beam splitter 407, to the fourth lens 411, which transmits the light to the third photodiode 412.

In the color filter 408, the transmittance or the reflectivity simply increases or decreases in proportion to the increase of the wavelength in a specific wavelength range. Here, the ratio of the transmittance divided by the reflectivity of incident light has one-to-one correspondence with the wavelength of incident light (see (b) of FIG. 5). The third and fourth lenses 409 and 411 are a condenser lens that condenses light, reflected from or transmitted through the color filter 408.

The second photodiode 410 of the output wavelength detector detects the intensity of the reflected light from the color filter 408, which is received through the third lens 409, and the third photodiode 412 of the output wavelength detector detects the intensity of the transmitting light, which is received from the color filter 408 through the fourth lens 411.

Figure 5:
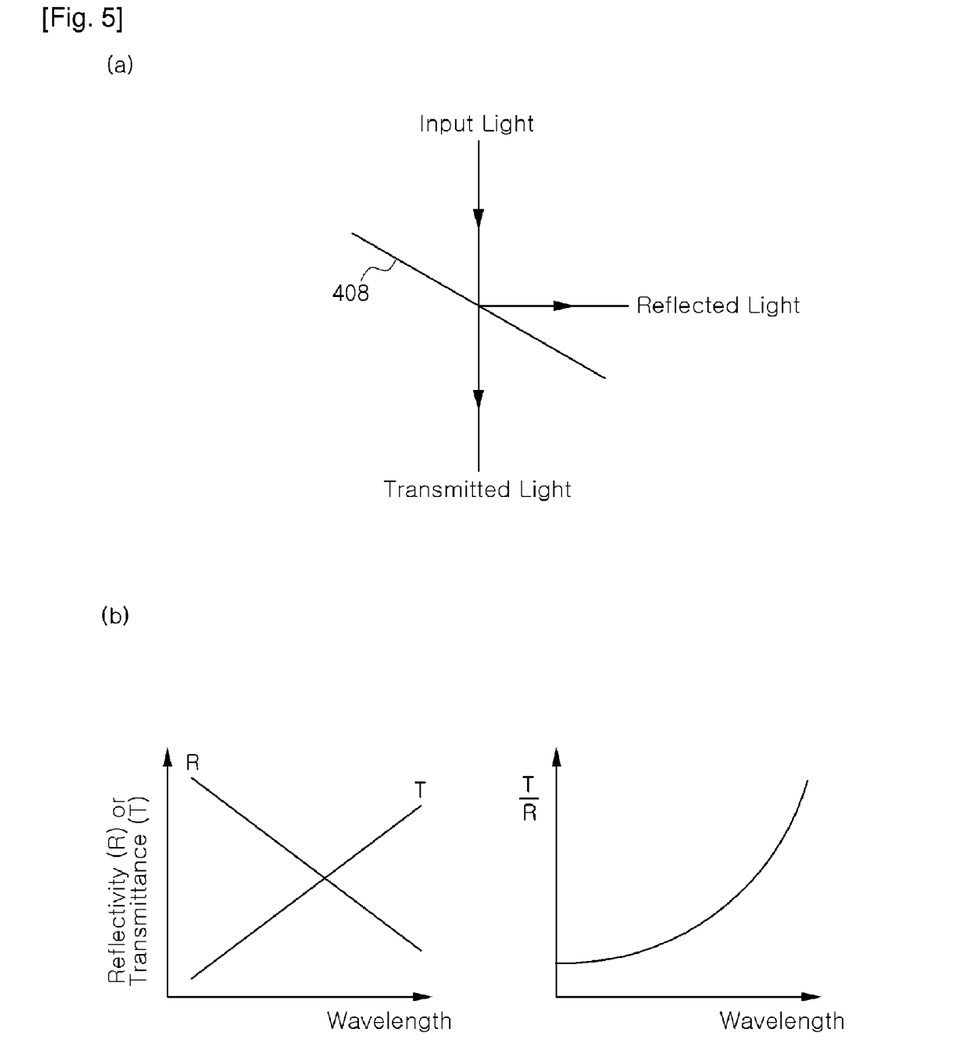
FIG. 5 is graphs illustrating the construction and output results of the color filter shown in FIG. 4.

In the portable measuring system having a biophotonic sensor of the present invention, the intensity of the transmitting light, detected by the third photodiode 412, is divided by the intensity of the reflected light, detected by the second photodiode 410, and the resultant ratio is compared with a graph of (b) of FIG. 5, which shows one-to-one correspondence between the transmittance/reflectivity T/R of the color filter 408 and the wavelength. In this way, the portable measuring system of the present invention can produce a correct output wavelength of the tunable light source 402.

In the biophotonic sensor 414, an antibody of an antigen to be detected is immobilized. According to the transmittance or the reflectivity determined by an antigen-antibody reaction, the biophotonic sensor 414 transmits or reflects the light, transmitted through the second beam splitter 407, to enter the fifth lens 415 or the second beam splitter 407.

Then, the fifth lens 415 condenses the light, transmitted through the biophotonic sensor 414, and sends the transmitting light to the fourth photodiode 416, which measures the intensity $P_4$ of the transmitting light.

The light reflected from the biophotonic sensor 414 is reflected again by the second beam splitter 407 to the sixth lens 417. The sixth lens 417 condenses the light, reflected from the second beam splitter 407, and sends the light to the fifth photodiode 418, which measures the intensity $P_3$ of the reflected light.

Each of the condenser lenses 405, 409, 411, 415 and 417 may be omitted if the light-receiving surface area of a corresponding one of the photodiodes 406, 410, 412, 416 and 418 is larger than the size of light beam.

Thus, it is possible to control the light output (intensity and wavelength) of the tunable light source 402 to be uniform by feeding back the output intensity $P_1$, detected by the first photodiode 406, and the output wavelength, detected by the second and third photo diodes 410 and 412, to the tunable light source controller 401.

The light from the tunable light source 402 is split into two beams at the first beam splitter 404, so that only a portion of the light is sent to the first photodiode 406. During this process, light loss takes place when the light passes through several optical elements.

When $P_2$ indicates light output intensity detected at the first photodiode 406, only a portion of light output intensity $P_0$ from the tunable light source 402 is sent to the first photodiode 406. The ratio $P_2/P_0$ can be easily measured by experiments. When this ratio is set to be a correction factor B, the actual light output intensity of the tunable light source 402 is produced by dividing the light output intensity $P_2$, detected by the first photodiode 406, with the correction factor B ($P_0=P_2/B$).

In addition, the light output intensity $P_0$ from the tunable light source 402 is split into two portions by the first beam splitter 404, and is split again into two portions by the second beam splitter 407, so that only a small portion of the light output intensity $P_0$ is sent to the biophotonic sensor 414.

The light passes through several optical elements from the tunable light source 402 to the biophotonic sensor 414, and thus light loss takes place during this passage. Since only a portion of the light output intensity $P_0$ from the tunable light source 402 is sent to the biophotonic sensor 414, a correction factor A should be considered. When $P_1$ is the light intensity sent to the biophotonic sensor 414, the correction factor A is $P_1/P_0$.

At the same reason, only a portion of the light, reflected by the biophotonic sensor 414, is sent to the fifth photodiode 418. When the light intensity reflected from the bio-photonic sensor 414 is $P_{ref}$, and the light intensity detected by the fifth photodiode 418 is $P_3$, $P_{ref}$ and $P_3$ make an equation: $P_3=C \times P_{ref}$, wherein C is the ratio of $P_3$ with respect to $P_{ref}$. The actual light intensity $P_{ref}$, reflected from the biophotonic sensor 414, is $P_3/C$.

In addition, light loss takes place when the light transmitted through the biophotonic sensor 414 is sent to the fourth photodiode 416 through the fifth lens 415. When the light intensity transmitted through the biophotonic sensor 41 is $P_{tran}$, and the light intensity detected by the fourth photodiode 416 is $P_4$, $P_{tran}$ and $P_4$ make an equation: $P_4=D \times P_{tran}$, where D is the ratio of $P_4$ with respect to $P_{tran}$, and $P_4/D$ is the actual light intensity $P_{tran}$, transmitted through the biophotonic sensor.

The above-mentioned correction factors A, B, C and D are necessary for measuring correct transmittance and reflectivity. The correction factors are influenced by the construction of the system, the characteristics of components used and so on, and can be easily determined by experiments. As an alternative, these correction factors may not be considered. This is because correct transmittance or reflectivity is not required when desired measurements are not correct transmittance and reflectivity, but are only maximum and minimum wavelength variations of reflectivity spectrum and transmittance spectrum as shown in FIG. 3.

According to the present invention, the actual intensity of light sent to the bio-photonic sensor 414 can be calculated using the intensity of light detected by the first photodiode 406. That is, an equation $$P_1 = \frac{A}{B} \times P_2$$

is obtained from equations $P_1=A \times P_0$ and $P_2=B \times P_0$.

Here, the transmittance of the biophotonic sensor 414 is $P_{tran}/P_1$, and using equations $$P_{tran} = \frac{P_4}{D}$$

and $$P_1 = \frac{A}{B} \times P_2,$$

transmittance can be calculated from $$\frac{B}{AD} \times \frac{P_4}{P_2}.$$

Next, the reflectivity of the biophotonic sensor is $P_{ref}/P_1$, and using equations $$P_{ref} = \frac{P_3}{C}$$

and $$P_1 = \frac{A}{B} \times P_2,$$

reflectivity can be calculated from $$\frac{B}{AC} \times \frac{P_3}{P_2}.$$

Therefore, the concentration of an antigen can be produced as follows: The transmittance spectrum and/or the reflectivity spectrum of the biophotonic sensor 414 prior to an antigen-antibody reaction is measured. The measurement result is compared with a temporal variation of the transmittance spectrum and/or the reflectivity spectrum of the biophotonic sensor 414 after the antigen-antibody reaction. The comparison result is used as a basis to determine whether or not a specific antigen is present and to measure the concentration of the antigen if present.

FIG. 5 is graphs illustrating the construction of the color filter 408 shown in FIG. 4, and characteristics curves of transmittance T and reflectivity R. The ratio of the transmittance with respect to the reflectivity T/R of the color filter has a one-to-one correspondence with the wavelength of incident light.

As shown in (a) of FIG. 5, the color filter 408 splits incident light into two beams by reflecting one beam and transmitting the other beam. The second photodiode 410 receives the reflected light from the color filter 408 through the third lens 409, thereby acquiring the reflectivity thereof. The third photodiode 412 receives the transmitting light from the color filter 408 through the fourth lens 411, thereby acquiring the transmittance thereof. The function shown in (b) of FIG. 5 is applied to the reflectivity and the transmittance acquired as above, thereby calculating the output wavelength of the tunable light source 402.

Since the characteristics curves of the transmittance T and the reflectivity R of the color filter shown in (b) of FIG. 5 represent unique characteristics of the color filter 408, the characteristics table of the color filter 408 may be prepared beforehand, and be installed, as a database, in the tunable light source controller 401. The output wavelength of the tunable light source 402 can be produced using the reflectivity and the transmittance acquired by the output wavelength detector.

The output wavelength of the tunable light source 402 can be measured using a spectrometer or an optical spectrum analyzer. However, the spectrometer and the optical spectrum analyzer are bulky, and thus are inadequate to attached to a portable system.

Figure 6:
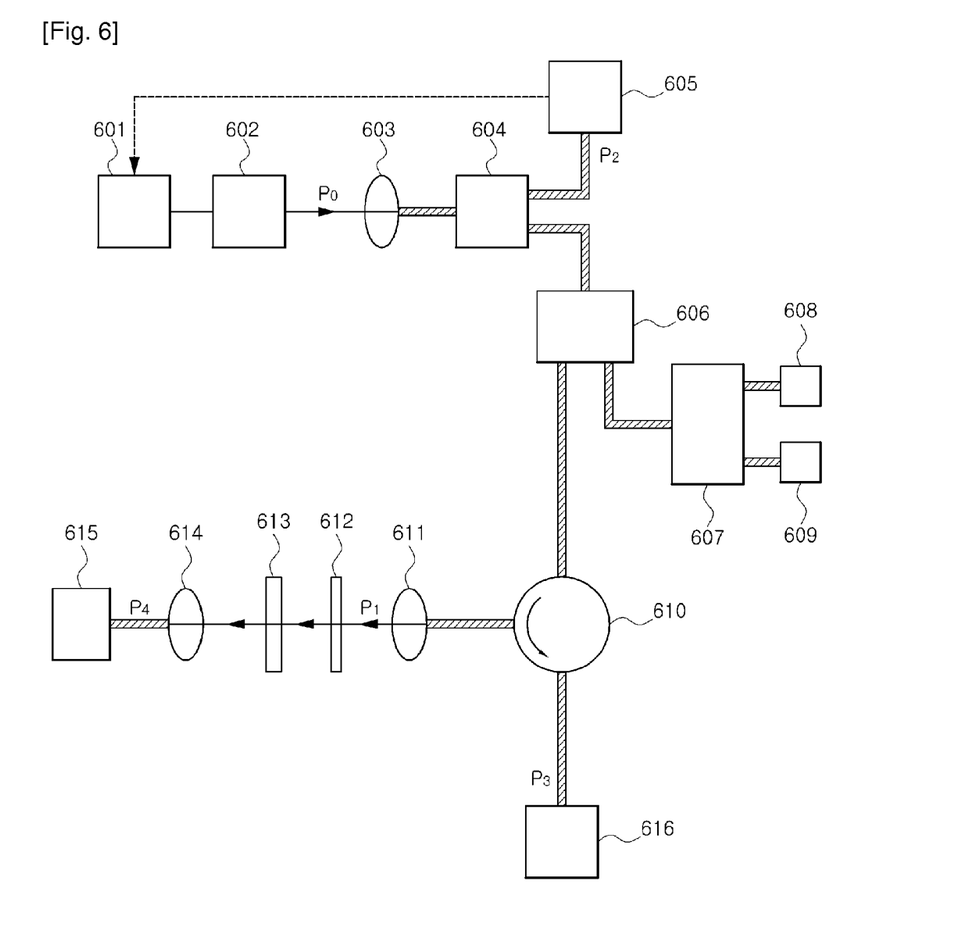
FIG. 6 is a construction view illustrating a portable measuring system having a bio-photonic sensor according to another embodiment of the present invention.

FIG. 6 is a construction view illustrating a portable measuring system having a bio-photonic sensor according to another embodiment of the present invention.

Referring to FIG. 6, the measuring system having a bio-photonic sensor of the present invention includes a tunable wavelength controller 601, a tunable light source 602, first to third lenses 603, 611 and 614, first and second optical fiber couplers 604 and 606, first to fifth photodiodes 605, 608, 609, 615 and 616, a polarization filter 612, a bio-photonic sensor 613, a Wavelength Division Multiplexing (WDM) coupler 607 and an optical fiber circulator 610. In this embodiment of the present invention, respective components are connected to each other via fiber optic cables, which are indicated by hatches in FIG. 6, and 1×2 type optical fiber couplers are used to split one beam into two beams.

Here, the light provider includes the tunable light source controller 601, the tunable light source 602 and the first lens 603, the first optical splitter includes the first optical fiber coupler 604, and the second optical splitter includes the second optical fiber coupler 606 and the optical fiber circulator 610. The output intensity detector includes the first photodiode 605, the output wavelength detector includes the WDM coupler 607 and the second and third photodiodes 608 and 609, the transmittance detector includes the third lens 613 and the fourth photodiode 614, and the reflectivity detector includes the fifth photodiode 615. The output intensity detector acts to detect the output intensity of the tunable light source 602, and the output wavelength detector acts to detect the output wavelength of the tunable light source 602.

Specifically, the tunable light source controller 601 supplies power to the tunable light source 602, and controls the output wavelength thereof.

The first lens 603 sends light from the tunable light source 601 to an optical fiber.

The first optical fiber coupler 604 splits light from the first lens 603 into two light beams, and sends one light beam to the first photodiode 605 and the other light beam to the second optical fiber coupler 606.

The first photodiode 605 detects the intensity of light, which is split by the first optical fiber coupler 604. The intensity of the split light corresponds to the output intensity $P_2$ of the tunable light source 602.

The present invention can maintain the output intensity of the tunable light source 602 to be uniform by feeding back the detected light intensity $P_2$ to the tunable light source controller 601. That is, the output intensity is maintained in such a degree that the light intensity does not rapidly change according to the wavelength in a wavelength range where reflectivity spectrum and transmittance spectrum are measured.

The second optical fiber coupler 606 splits light from the first optical fiber coupler 604 into two beams, and sends one light beam to the output wavelength detector, which includes the WDM coupler 607 and the second and third photodiodes 608 and 609, and the other light beam to the optical fiber circulator 610. Here, the optical fiber circulator 610 sends light from the second optical fiber coupler 606 to only the bio-photonic sensor 613, and sends light reflected from the biophotonic sensor 613 to only the fifth photodiode 616. That is, the optical fiber circulator 610 prevents light, reflected from the biophotonic sensor 613, from returning to the second optical fiber coupler 606.

The polarization filter 612 allows light of a specific polarization to enter the bio-photonic sensor 613. Alternatively, the polarization filter may be omitted if the transmittance spectrum and the reflectivity spectrum of the biophotonic sensor are not polarization dependent.

The second lens 611 converts light, introduced through the optical fiber circulator 610, into parallel light, and sends the parallel light to the biophotonic sensor 613. In the biophotonic sensor 613, an antibody of an antigen, which is supposed to be detected, is immobilized. The biophotonic sensor 613 transmits or reflects incident light according to the transmittance and the reflectivity thereof, which are determined by the reaction between the antigen and the antibody.

The third lens 614 condenses light, transmitted through the biophotonic sensor 613, and the fourth photodiode 615 detects the intensity of light, introduced from the third lens 614. The third lens 614 may be omitted if the light-receiving surface area of the fourth photodiode 615 is larger than the size of light beam. The fiber optic cable between the third lens 614 and the fourth photodiode 615 may also be omitted.

The light reflected from the biophotonic sensor 613 is sent to only the fifth photodiode 616 through the optical fiber circulator 610. The fifth photodiode 616 detects the intensity of the light reflected from the biophotonic sensor 613.

Referring to FIG. 6, $P_0$ indicates the light output intensity of the tunable light source 602, $P_2$ indicates the intensity of light detected by the first photodiode 605, $P_1$ indicates the intensity of light sent to the biophotonic sensor 613, $P_4$ indicates the intensity of light sent to the fourth photodiode 615, $P_3$ indicates the intensity of light sent to the fifth photodiode 616, $P_{tran}$ indicates the intensity of light transmitted through the bio-photonic sensor 613, and $P_{ref}$ indicates the intensity of light reflected from the bio-photonic sensor 613.

The light emitted from the tunable light source 602 is split into two beams through the first and second optical fiber couplers 604 and 606 and the WDM coupler 607. Since light loss takes place when the light is passing through the lenses and optical fibers, it is necessary to consider correction factors. When $P_0$, $P_1$, $P_2$, $P_3$, $P_4$, $P_{tran}$, and $P_{ref}$ are defined as shown in FIG. 6, the definitions of the correction factors may be the same as those in FIG. 4.

Accordingly, the intensity of light actually sent to the biophotonic sensor 613 can be calculated using the intensity of light detected by the first photodiode 605. An equation $$P_1 = \frac{A}{B} \times P_2$$

is obtained based upon equations $P_1 = A \times P_0$ and $P_2 = B \times P_0$.

Here, the transmittance of the biophotonic sensor 613 is $P_{tran}/P_1$, and using equations $$P_{tran} = \frac{P_4}{D}$$

and $$P_1 = \frac{A}{B} \times P_2,$$

transmittance can be calculated from $$\frac{B}{AD} \times \frac{P_4}{P_2}.$$

Next, the reflectivity of the biophotonic sensor 613 is $P_{ref}/P_1$, and using equations $$P_{ref} = \frac{P_3}{C}$$

and $$P_1 = \frac{A}{B} \times P_2,$$

reflectivity can be calculated from $$\frac{B}{AC} \times \frac{P_3}{P_2}.$$

Therefore, the concentration of an antigen can be produced as follows: The transmittance spectrum and/or the reflectivity spectrum of the biophotonic sensor 613 prior to an antigen-antibody reaction is measured.

The measurement result is compared with a temporal variation of the transmittance spectrum and/or the reflectivity spectrum of the biophotonic sensor 613 after the antigen-antibody reaction. The comparison result is used as a basis to determine whether or not a specific antigen is present and to measure the concentration of the antigen if present.

Figure 7:
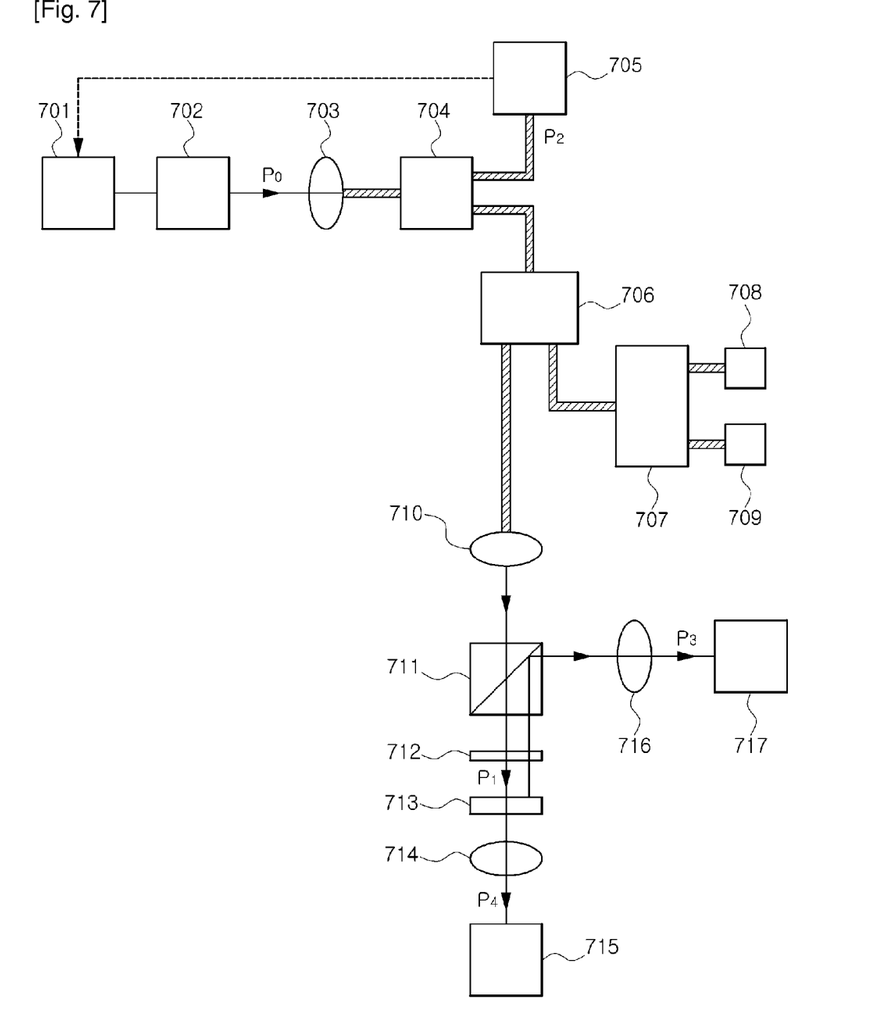
FIG. 7 is a construction view illustrating a portable measuring system having a bio-photonic sensor according to a further embodiment of the present invention.

FIG. 7 is a construction view illustrating a portable measuring system having a bio-photonic sensor according to a further embodiment of the present invention, in which a beam splitter replaces the optical fiber circulator of the portable measuring system shown in FIG. 6.

Referring to FIG. 7, the portable measuring system having a biophotonic sensor includes a tunable light source controller 701, a tunable light source 702, first to fourth lenses 703, 710, 714 and 716, first and second optical fiber couplers 704 and 706, first to fifth photodiodes 705, 708, 709, 715 and 717, a polarized light filter 712, a bio-photonic sensor 713, a WDM coupler 707 and a beam splitter 711. In this embodiment of the present invention, respective components are connected to each other via fiber optic cables, which are indicated by hatches in FIG. 6, and 1×2 type optical fiber couplers are used to split one beam into two beams. The components 701 to 709 of FIG. 7 are substantially the same as the components 601 to 609 of FIG. 6.

Here, the light provider includes the tunable light source controller 701, the tunable light source 702 and the first lens 703, the first optical splitter includes the first optical fiber coupler 704, and the second optical splitter includes the second optical fiber coupler 706, the second lens 710 and the beam splitter 711. The output intensity detector includes the first photodiode 705, the output wavelength detector includes the WDM coupler 707 and the second and third photodiodes 708 and 709, the transmittance detector includes the third lens 714 and the fourth photodiode 715, and the reflectivity detector includes the fourth and fifth photodiodes 715. The output intensity detector acts to detect the output intensity of the tunable light source 702, and the output wavelength detector acts to detect the output wavelength of the tunable light source 702.

Specifically, the tunable light source controller 701 supplies power to the tunable light source 702, and controls the output wavelength thereof.

The first lens 703 sends light from the tunable light source 701 to an optical fiber.

The first optical fiber coupler 704 splits light from the first lens 703 into two light beams, and sends one light beam to the first photodiode 705 and the other light beam to the second optical fiber coupler 706.

The first photodiode 705 detects the intensity of light, which is split by the first optical fiber coupler 704. The intensity of the split light is proportional to the output intensity $P_2$ of the tunable light source 702.

The present invention can maintain the output intensity of the tunable light source 702 to be uniform by feeding back the detected light intensity $P_2$ to the tunable light source controller 701. That is, the output intensity is maintained in such a degree that the light intensity does not rapidly change according to the wavelength in a wavelength range where reflectivity spectrum and transmittance spectrum are measured.

The second optical fiber coupler 706 splits light from the first optical fiber coupler 704 into two beams, and sends one light beam to the output wavelength detector, which includes the WDM coupler 707 and the second and third photodiodes 708 and 709, and the other light beam to the beam splitter 711.

The second lens 710 converts light, introduced through the optical fiber coupler 706, into parallel light, and sends the parallel light to the biophotonic sensor 713 through the beam splitter 711 and the polarized light filter 712. In the biophotonic sensor 713, an antibody of an antigen, which is supposed to be detected, is immobilized. The bio-photonic sensor 713 transmits or reflects incident light according to the transmittance and the reflectivity thereof, which are determined by the reaction between the antigen and the antibody.

The third lens 714 condenses the light, transmitted through the biophotonic sensor 713, and the fourth photodiode 715 detects the intensity of light, introduced from the third lens 714. The third lens 714 may be omitted if the light-receiving surface area of the fourth photodiode 715 is larger than the size of light beam.

The reflected light from the biophotonic sensor 713 is reflected again from the beam splitter 711, and is sent to the fifth photodiode 717 through the fourth lens 716. The fifth photodiode 717 detects the intensity of the light, reflected from the biophotonic sensor 713.

Referring to FIG. 7, $P_0$ indicates the light output intensity of the tunable light source 702, $P_2$ indicates the intensity of light detected by the first photodiode 705, $P_1$ indicates the intensity of light sent to the biophotonic sensor 713, $P_4$ indicates the intensity of light sent to the fourth photodiode 715, $P_3$ indicates the intensity of light sent to the fifth photodiode 716, $P_{tran}$ indicates the intensity of light transmitted through the bio-photonic sensor 713, and $P_{ref}$ indicates the intensity of light reflected from the bio-photonic sensor 713.

As in FIG. 6, the light emitted from the tunable light source 702 is split into two beams through the first and second optical fiber couplers 704 and 706 and the WDM coupler 707. Since light loss takes place when the light is passing through the lenses and optical fibers, it is necessary to consider correction factors. Here, the definitions of the correction factors may be the same as those in FIG. 4.

Accordingly, the intensity of light, which is actually sent to the biophotonic sensor 713, can be calculated using the intensity of light detected by the first photodiode 705. An equation $$P_1 = \frac{A}{B} \times P_2$$

is obtained based upon equations $P_1 = A \times P_0$ and $P_2 = B \times P_0$.

Here, the transmittance of the biophotonic sensor 713 is $P_{tran}/P_1$, and using equations $$P_{tran} = \frac{P_4}{D}$$

and $$P_1 = \frac{A}{B} \times P_2,$$

transmittance can be calculated from $$\frac{B}{AD} \times \frac{P_4}{P_2}.$$

Next, the reflectivity of the biophotonic sensor 713 is $P_{ref}/P_1$, using equations $$P_{ref} = \frac{P_3}{C}$$

and $$P_1 = \frac{A}{B} \times P_2,$$

reflectivity can be calculated from $$\frac{B}{AC} \times \frac{P_3}{P_2}.$$

Therefore, the concentration of an antigen can be produced as follows: The transmittance spectrum and/or the reflectivity spectrum of the biophotonic sensor 713 prior to an antigen-antibody reaction is measured. The measurement result is compared with a temporal variation of the transmittance spectrum and/or the reflectivity spectrum of the biophotonic sensor 713 after the antigen-antibody reaction. The comparison result is used as a basis to determine whether or not a specific antigen is present and to measure the concentration of the antigen if present.

Figure 8:
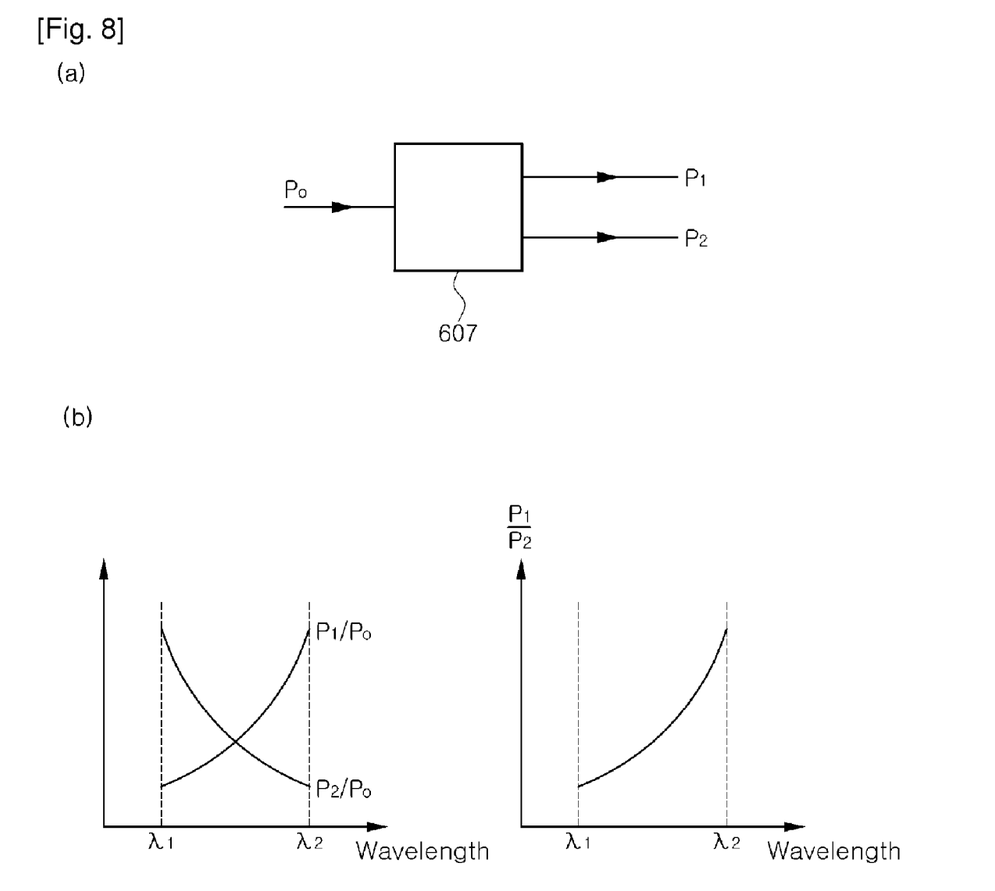
FIG. 8 is graphs illustrating the construction and output result of the WDM coupler shown in FIGS. 6 and 7.

FIG. 8 is graphs illustrating the construction of the WDM coupler 607 shown in FIG. 6, and wavelength characteristics according to output values of the WDM coupler 607.

Referring to (a) of FIG. 8, the WDM coupler 607 receives light through an input port and divides the light into two beams through two output ports. The output ports are optical fiber couplers, which have the largest transmittances at specific wavelengths $\lambda_1$ and $\lambda_2$.

Referring to graphs shown in (b) of FIG. 8, in a wavelength range from $\lambda_1$ to $\lambda_2$, $P_1$ indicates an output through port 1, and $P_2$ indicates an output through port 2. Here, $P_1/P_2$ or $P_2/P_1$ is a one-to-one function of input wavelengths. Accordingly, a preset value $P_1/P_2$ or $P_2/P_1$ of the WDM coupler 607 is compared with the light output, measured by the second and third photodiodes 608 and 609, thereby calculating the output wavelength of the tunable light source 602.

While the present invention has been described with reference to the particular illustrative embodiments and the accompanying drawings, it is not to be limited thereto but will be defined by the appended claims. It is to be appreciated that those skilled in the art can substitute, change or modify the embodiments in various forms without departing from the scope and spirit of the present invention.

The invention claimed is:

1. A portable measuring system having a biophotonic sensor comprising:
    a light provider configured to emit light;
    a first optical splitter configured to split the light emitted from the light provider into first and second paths;
    an output intensity detector configured to detect an output intensity of the light on the first path;
    a second optical splitter configured to split the light on the second path, into third and fourth paths;
    an output wavelength detector configured to detect an output wavelength of the light on the third path:
    the biophotonic sensor is configured to transmit or reflect the light on the fourth path, wherein the light intensity on the fourth path changes based on an antigen-antibody reaction in the biophotonic sensor;
    a transmittance detector configured to detect an intensity of the light transmitted through the biophotonic sensor; and
    a reflectivity detector configured to detect an intensity of the light reflected from the biophotonic sensor,
    wherein the light provider comprises:
    a tunable light source; and
    a tunable light source controller configured to control power supplied to the tunable light source based on the output intensity of the light on the first path that is detected by the output intensity detector, and further configured to control an output wavelength of the tunable light source to be uniform based on the output wavelength of the light on the third path that is detected by the output wavelength detector.

2. The portable measuring system of claim 1, the portable measuring system further comprising:
    a polarized light filter disposed in the fourth path and configured to selectively provide light of a specific polarization to the biophotonic sensor.

3. A portable measuring system having a biophotonic sensor comprising:
    a light provider configured to emit light;
    a first optical splitter configured to split the light emitted from the light provider into first and second paths;
    an output intensity detector configured to detect an output intensity of the light on the first path;
    a second optical splitter configured to split the light on the second path, into third and fourth paths;
    an output wavelength detector configured to detect an output wavelength of the light on the third path;
    the biophotonic sensor is configured to transmit or reflect the light on the fourth path, wherein the light intensity on the fourth path changes based on an antigen-antibody reaction in the biophotonic sensor;
    a transmittance detector configured to detect an intensity of the light transmitted through the biophotonic sensor; and
    a reflectivity detector configured to detect an intensity of the light reflected from the biophotonic sensor, wherein the light provider comprises:

a tunable light source;

a tunable light source controller configured to control power supplied to the tunable light source based on the output intensity of the light on the first path that is detected by the output intensity detector, and further configured to control an output wavelength of the tunable light source to be uniform based on the output wavelength of the light on the third path that is detected by the output wavelength detector; and a lens configured to convert the light emitted from the tunable light source into parallel light.

4. The portable measuring system of claim 3, wherein the output intensity detector comprises a photodiode.

5. The portable measuring system of claim 4, wherein the output intensity detector further comprises a condenser lens configured to condense the light on the first path, and provide the condensed light to the photodiode.

6. The portable measuring system of claim 3, wherein each of the transmittance detector and the reflectivity detector comprises a photodiode configured to measure an intensity of the light, which is transmitted through or reflected from the biophotonic sensor.

7. The portable measuring system of claim 6, wherein the transmittance detector or the reflectivity detector comprises a condenser lens configured to condense the light, transmitted through or reflected from the biophotonic sensor, and provide the condensed light to the photodiode.

8. The portable measuring system of claim 3, wherein each of the first optical splitter and the second optical splitter comprises a 1×2 type beam splitter configured to split incident light into transmitting light and reflecting light.

9. The portable measuring system of claim 8, wherein the output wavelength detector comprises:

a color filter configured to split the light on the third path, into reflecting light and transmitting light;

a reflectivity detector of the color filter configured to detect an intensity of the light reflected from the color filter; and a transmittance detector of the color filter configured to detect an intensity of the light transmitted through the color filter.

10. The portable measuring system of claim 9, wherein each of the reflectivity detector and the transmittance detector of the color filter comprises a photodiode configured to detect an intensity of light.

11. The portable measuring system of claim 10, wherein each of the reflectivity detector and the transmittance detector of the color filter further comprises a condenser lens configured to condense incident light and provide the condensed light to the photodiode thereof.

12. The portable measuring system of claim 3, wherein the first optical splitter comprises a 1×2 type first optical fiber coupler configured to split incident light into two beams.

13. The portable measuring system of claim 12, wherein the output wavelength detector comprises:

a wavelength division multiplexing coupler configured to split the light on the third path into fifth and sixth paths;

a second photodiode configured to detect an intensity of the light on the fifth path; and a third photodiode configured to detect an intensity of the light on the sixth path.

14. The portable measuring system of claim 13, wherein the second optical splitter comprises:

a 1×2 type second optical fiber coupler configured to split the light on the second path into the third and the fourth paths; and an optical fiber circulator configured to provide the light on the fourth path to the biophotonic sensor, and provide the light reflected from the biophotonic sensor to the reflectivity detector.

15. The portable measuring system of claim 14, wherein the second optical splitter further comprises a lens configured to convert the light passing through the optical fiber circulator into parallel light and then provide the parallel light to the biophotonic sensor.

16. The portable measuring of claim 13, wherein the second optical splitter comprises:

a 1×2 type second optical fiber coupler configured to split the light provided from the 1×2 type first optical fiber coupler into the third and fourth paths; and a lens configured to convert the light on the fourth path into parallel light; and a 1×2 type beam splitter configured to split the parallel light into transmitting light and reflecting light.

* * * * *